United States Patent
Urich (10) Patent No.: US 6,966,894 B1
(45) Date of Patent: Nov. 22, 2005

(54) SYRINGES AND INJECTORS INCORPORATING MECHANICAL FLUID AGITATION DEVICES

(75) Inventor: Klaus Urich, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/763,646

(22) PCT Filed: Aug. 26, 1999

(86) PCT No.: PCT/EP99/06290

§ 371 (c)(1), (2), (4) Date: Jul. 9, 2001

(87) PCT Pub. No.: WO00/12158

PCT Pub. Date: Mar. 9, 2000

(30) Foreign Application Priority Data

Aug. 28, 1998 (DE) .............................. 198 40 532

(51) Int. Cl.⁷ ...................... A61M 37/00; A61M 5/315; A61M 31/00; A61M 5/00
(52) U.S. Cl. ...................... 604/154; 604/218; 604/500; 600/432
(58) Field of Search ........................ 604/82–92, 187, 604/218, 232, 403, 416, 154, 500; 600/432; 422/99, 100, 102; 206/220; 366/129–130

(56) References Cited

U.S. PATENT DOCUMENTS

| | | | |
|---|---|---|---|
| 3,604,417 A | | 9/1971 | Stolzenberg |
| 3,789,670 A | * | 2/1974 | Rosenwald .................. 366/140 |
| 3,831,903 A | | 8/1974 | Harmel, Jr. |
| 3,880,138 A | | 4/1975 | Wootten et al. |
| 4,006,736 A | * | 2/1977 | Kranys et al. ............... 600/432 |
| 4,008,718 A | | 2/1977 | Pitesky |
| 4,172,457 A | | 10/1979 | Choksi et al. |
| 4,687,000 A | | 8/1987 | Eisenhardt et al. |
| 4,784,297 A | | 11/1988 | Katz |
| 4,846,786 A | | 7/1989 | Freed et al. |
| 5,108,927 A | * | 4/1992 | Dorn .......................... 435/243 |
| 5,139,490 A | * | 8/1992 | Vetter et al. ................ 604/201 |
| 5,240,322 A | | 8/1993 | Haber et al. |
| 5,246,670 A | * | 9/1993 | Haber et al. ................ 422/102 |
| 5,352,036 A | | 10/1994 | Haber et al. |
| 5,360,410 A | | 11/1994 | Wacks |
| 5,383,858 A | * | 1/1995 | Reilly et al. ................ 604/131 |

(Continued)

FOREIGN PATENT DOCUMENTS

DE      296 22 313      3/1977

(Continued)

OTHER PUBLICATIONS

"Selective Destruction of Contrast Agent Microspheres," Bouakaz, et al., IEEE Ultrasonics Symposium, pp. 1693-1696, (1999).

(Continued)

Primary Examiner—Nicholas D. Lucchesi
Assistant Examiner—Catherine S. Williams
(74) Attorney, Agent, or Firm—Gregory L. Bradley (57) ABSTRACT

A syringe for use with an injector includes a body comprising a distal discharge end, a plunger movably disposed within the body, and an agitation element disposed within the body between the plunger and the distal discharge end. A movement mechanism is operably associated with the injector to move the syringe in such a way that the at least one agitation element agitates a fluid contained in the syringe. Preferably, the syringe contains an ultrasound contrast agent that is agitated by the agitation element. An injector system and a method for agitating the contents of a syringe are also provided.

111 Claims, 6 Drawing Sheets

U.S. PATENT DOCUMENTS

| | | |
|---|---|---|
| 5,401,253 A | 3/1995 | Reynolds |
| 5,425,580 A | 6/1995 | Beller |
| 5,469,849 A | 11/1995 | Sasaki et al. |
| 5,528,923 A | 6/1996 | Ledez et al. |
| 5,601,086 A | 2/1997 | Pretlow, III et al. |
| 5,611,344 A * | 3/1997 | Bernstein et al. ............ 600/458 |
| 5,686,060 A | 11/1997 | Schneider et al. |
| 5,806,519 A | 9/1998 | Evans, III et al. |
| 5,840,026 A | 11/1998 | Uber, III et al. |
| 5,846,517 A | 12/1998 | Unger |
| 6,317,623 B1 * | 11/2001 | Griffiths et al. ............. 600/431 |

FOREIGN PATENT DOCUMENTS

| | | |
|---|---|---|
| DE | 34 11 427 | 10/1985 |
| DE | 39 34 024 | 4/1991 |
| DE | 196 25 102 | 8/1997 |
| EP | 0 033 292 | 7/1984 |
| EP | 0 770 352 | 5/1997 |
| WO | WO 96/18420 | 6/1996 |
| WO | WO 97/18845 | 5/1997 |
| WO | WO 98/22168 | 5/1998 |
| WO | WO 98/33538 | 8/1998 |
| WO | WO 99/27981 | 6/1999 |
| WO | WO 00/12157 | 3/2000 |
| WO | WO 00/12158 | 3/2000 |
| WO | WO 00/53242 | 9/2000 |

OTHER PUBLICATIONS

"Effect of Ultrasound on the Release of Micro-Encapsulated Drugs," Frinking, et al., Ultrasonics 36, pp. 709-712, (1998).

"A Particulate Contrast Agent With Potential for Ultrasound Imaging of Liver," Parker, et al., Ultrasound in Med. & Biol., vol. 13, No. 9, pp. 555-566 (1987).

International Search Report for Counterpart PCT Application No. PCT/EP99/06290.

* cited by examiner

SYRINGES AND INJECTORS INCORPORATING MECHANICAL FLUID AGITATION DEVICES

BACKGROUND OF THE INVENTION

The present invention relates generally to movement devices for agitating the contents of syringes and, more particularly, to syringes and injectors incorporating movement devices for agitating contrast agents disposed within the syringes.

Syringes which are prefilled with ultrasound contrast agents are clamped into injectors for injection. The syringes remain therein for several minutes to one or more hours. The duration of one or more injections, including the intervening periods between the injections, may last for more than 10 minutes. Depending on the nature and composition of the contrast agent, dissociation commences at different times. During this period, the ultrasound contrast agent becomes dissociated and the phases are separated from one another. The ultrasound contrast agent as a whole is no longer homogeneous. In order to restore this homogeneity, the entire injector, including the syringe clamped therein, is moved manually. Movements of this nature are not reproducible, and sufficient homogenization is not ensured.

Ultrasound contrast agents are sensitive to transverse forces. Under excessively high forces, the particles are torn apart and destroyed. This impairs the quality of the ultrasound contrast agent. Thus, to maintain the suspension of particles in ultrasound contrast agents it is necessary to agitate the agents, but at the same time the particles must not be destroyed by the agitation.

Ultrasound contrast agents are generally described in Supplement to Diagnostic Imaging, May 1995, Advanced Ultrasound, Editor: Peter L. OGLE, Editorial Offices: 600 Harrison St. San Francisco, Calif. 94107 USA.

Glass syringes and plastic syringes are described extensively in the publication by Junga (M. JUNGA (1973) Pharm. Ind. Vol. 35, No. IIa, pages 824 to 829). A mixture of glass and plastic is described in PCT Publication No. WO 96/00098.

Injectors are generally described in EP Publication No. 0 584 531.

SUMMARY OF THE INVENTION

The present invention provides apparatuses and methods for maintaining the homogeneity and integrity of an ultrasound contrast agent over a relatively long period of time without destroying the consistency of the ultrasound contrast agent and hence impairing its pharmacological and diagnostic properties. The dissociation begins immediately after the initial preparation of the ultrasound contrast agent, and at the latest after the syringe has been inserted into the injector when the latter is at rest (i.e., is not moving). By maintaining the homogeneity and integrity of the particles suspended in the contrast agent at optimal levels, the diagnostic properties of the contrast agent can be optimized.

The present invention further provides apparatuses and methods for continuous, controlled and/or reproducible agitation procedures for contrast agents. These procedures can be utilized between the time of preparation of the contrast agents and their injection into a patient.

Further, the present invention provides agitation procedures that can be specifically designed and/or adjusted for specific contrast agents, including ultrasound contrast agents.

Also, the agitation procedures may be designed to minimize turbulent agitation of the contrast agents, thereby reducing shear forces and other stresses that could be harmful to the integrity of the particles suspended in the contrast agents.

Moreover, the present invention provides a controlled application of magnetic energy to maintain the homogeneity of the contrast agent suspension, without mixing or otherwise destroying the particles of the contrast agents.

One aspect of the present invention is achieved by means of a syringe which is filled with ultrasound contrast agent for administering the contents thereof by means of an injector, wherein at least one agitation element is contained in the syringe. The agitation element can be present as a solid or a gas, and preferably has a different density from that of the ultrasound contrast agent. Preferably, the syringe is movable with respect to the lines of gravity by means of the injector or an accessory thereto.

Another aspect of the present invention is achieved by means of an injector, or an accessory therefore, that moves a syringe mounted thereon for inducing at least one agitation element disposed within the syringe to agitate the contents thereof. The at least one agitation element may be present in the syringe in a solid or a gas phase, and preferably has a density different from that of the ultrasound contrast agent.

In a preferred embodiment, the movements of the syringe are circular, partially circular or linear. The movements of the syringe must be such that the agitation element disposed within the syringe moves with respect thereto. Typical movements contemplated by the present invention include pitching, swaying, yawing and shaking. All linear movements with a horizontal vector are also included. Movements along the lines of gravity typically do not induce any mixing or homogenization of the contrast agent contained within the syringe. Only when a movement component which does not run exclusively along the lines of gravity is added does homogenization of the contrast agent become possible. Preferably, the movements are rotational movements, the axis of rotation of which may be arranged as desired.

In a preferred embodiment, the present invention provides a combination of a syringe filled with a contrast agent and an injector or an accessory for use with an injector. At least one agitation element is contained in the syringe, is present as a gas or a solid and has a density different from that of the contrast fluid. The syringe is movable with respect to the lines of gravity by means of the injector or the accessory therefore.

Preferably, the syringes are made from plastic, glass or plastic/glass. Furthermore, the syringe are preferably disposable syringes.

The agitation element may be a gas or a solid body, the density of which differs from that of the ultrasound contrast agent. Preferably, the agitation element comprises a solid body with a density that is higher than that of the ultrasound contrast agent. The agitation element can move in the syringe under the force of gravity, by the syringe being moved about, for example, one of its axes.

To accomplish this movement, the injector adjusts and/or moves the syringe by means of a tilting movement with respect to the longitudinal axis thereof. Preferably, the injector is mounted in such a way that the mounted, approximately horizontally-arranged syringe is moved about this position, the center of rotation preferably lying outside the syringe and the axis of rotation being perpendicular to the longitudinal axis of the syringe.

The present invention, along with further aspects and attendant advantages, will best be understood by reference to the following detailed description taken in conjunction with the accompanying drawings.

DETAILED DESCRIPTION OF THE PRESENTLY PREFERRED EMBODIMENTS

Figure 1:
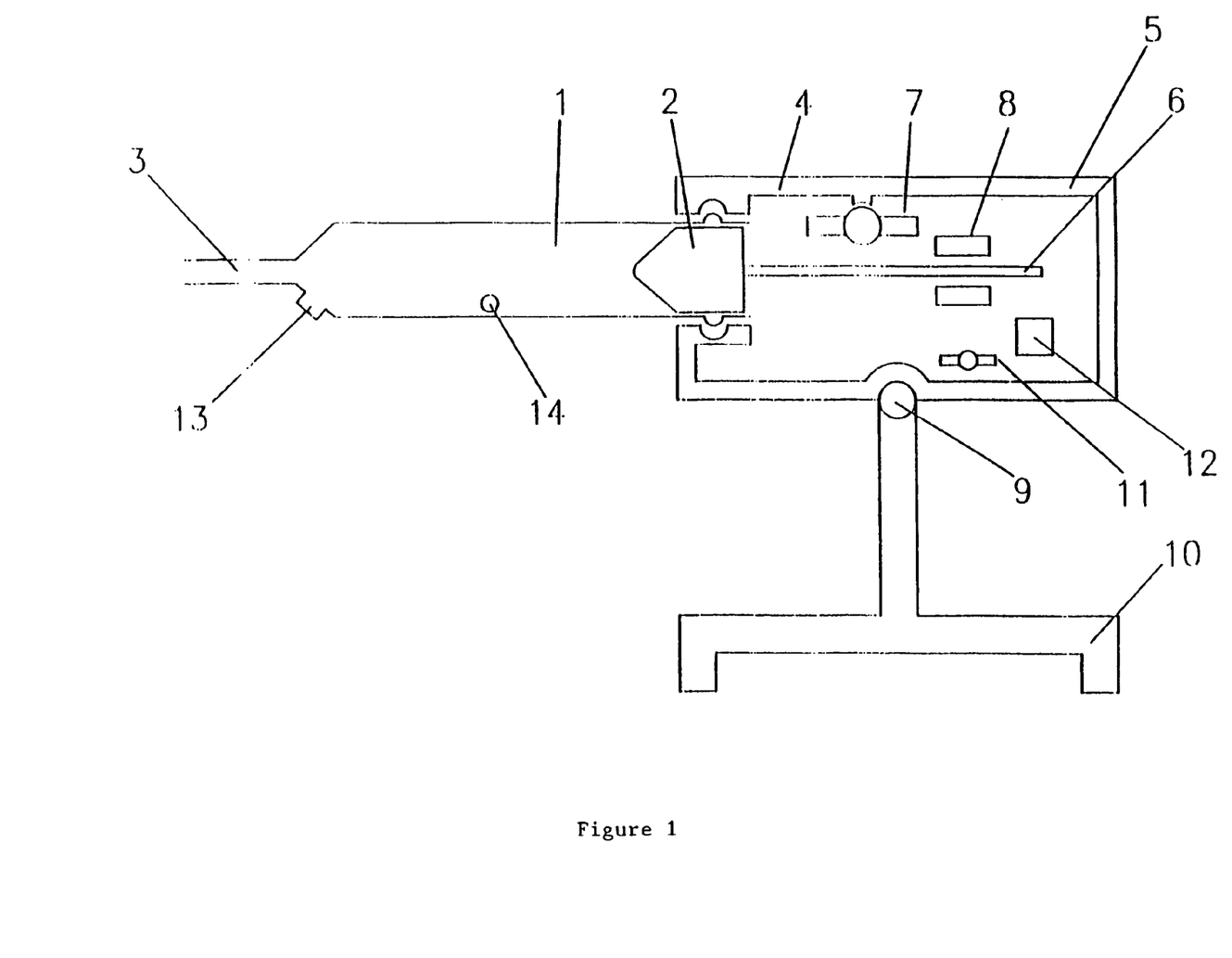
FIG. 1 is an elevated, cross-sectional view of an injector system incorporating a rotation device between the injector stand and the injector housing.
Figure 2:
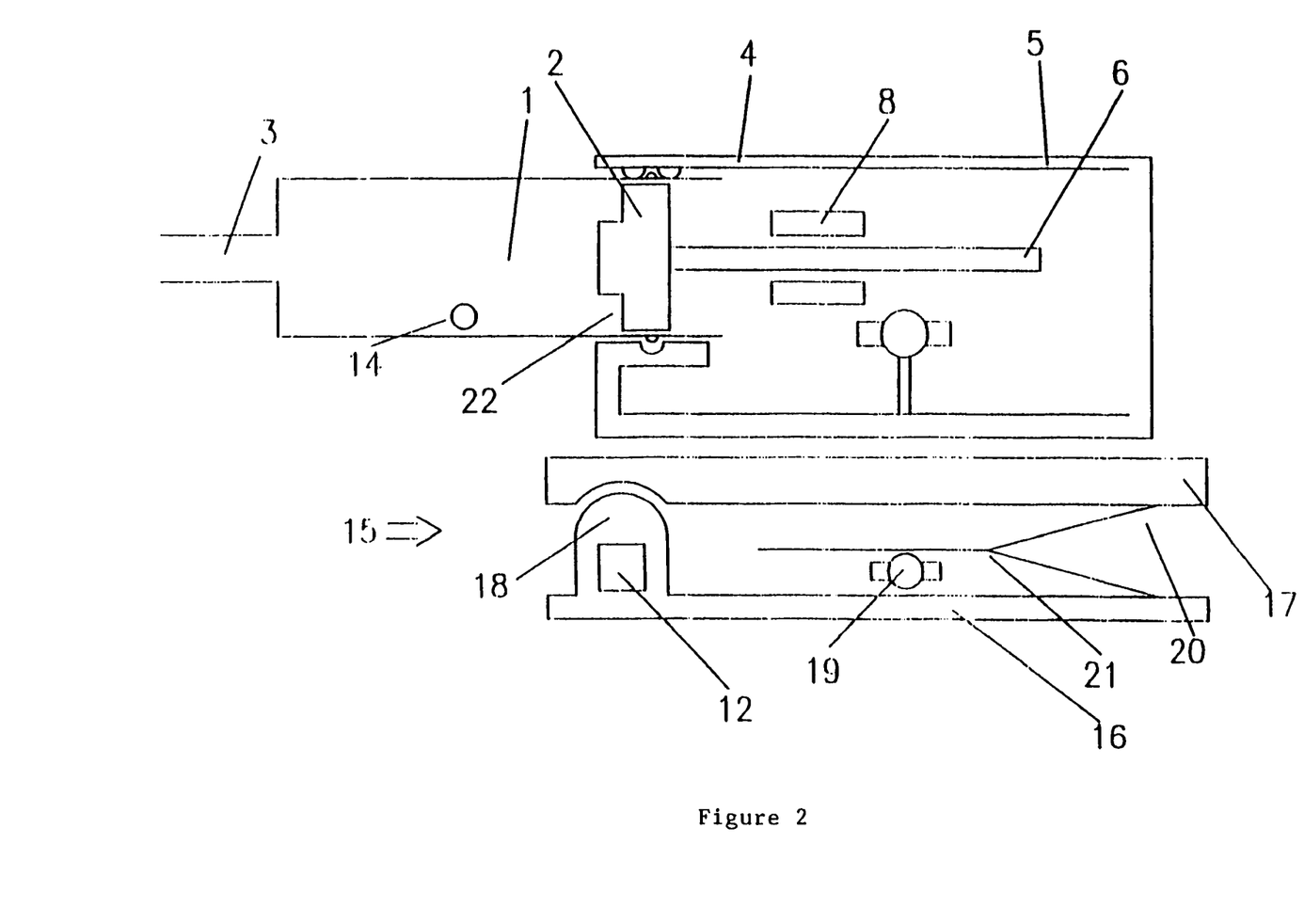
FIG. 2 is an elevated, cross-sectional view of an injector system incorporating an accessory for tilting the injector and syringe mounted thereon.

Before turning to a detailed description of the preferred embodiments, as illustrated in FIGS. 1 and 2, the present invention is described first below in general terms applicable to all suitable embodiments thereof.

As an initial matter, the terms "syringe" and/or "syringes" as used herein can mean and encompass the following terms and devices: cartridges (large-volume syringe with a volume of at least 100 ml); ampoule syringes; disposable syringes; disposable syringe ampoules; throw-away syringe ampoules; throw-away syringes; injection ampoules; disposable injection ampoules; ready-for-injection ampoules; cylindrical ampoules; twin-chamber injection ampoules; two-chamber syringes; two-chamber syringe ampoules; and no-delay syringes.

In addition, the terms "injector" and/or "injectors" as used herein can mean and encompass the following terms and devices: infusion pumps; infusers; perfusors; and all other applicators or devices that operate to empty syringes of fluid contain therein.

Further, the terms "accessory" and/or "accessories" as used herein can mean and encompass the following: all devices which are or may be physically connected to an injector and assume the role of moving the entire injector or parts thereof in such a way that the syringe changes position. Typical accessories include tables which execute a wobbling movement or a rocking movement and on which the injectors are positioned. Further accessories may include a shaft, for example, a motor-drive shaft, that is attached to the stand of the injector and changes the position of the syringe. In this case, the syringe, a holder for the syringe, the ram and the ram-moving device (e.g., a motor) are usually rigidly connected to one another. The essential factor is that the injector or the accessory therefor moves at least the syringe with respect to the standing surface or suspension mount of the injector or of the accessory.

In the present invention, the agitation element may be encased by various substances. Suitable substances for the casing include, but are not limited to, glass and plastic materials, such as Teflon, which are preferably inert with respect to contrast agents. The use of a casing also reduces friction, which results in a reduction in or avoidance of particles within the syringe. Preferably, the agitation element is in the form of a ball. It is also possible for the gas to be surrounded by a cover, as is found with floats or immersed bodies.

The syringe preferably includes a recess therein for accommodating the agitation element. The recess preferably is designed in such a way that the agitation element can slide into or out of the recess. The recess preferably lies outside the movement range of the plunger in the syringe or itself forms part of the plunger.

Also, the recess may be formed both in the syringe and in the plunger. Preferably, the recess is positioned at or adjacent to the distal end (i.e., the syringe end having the needle attachment, hose attachment or luer lock fitting) of the syringe.

Further, the recess may be situated in the distal cover of the syringe cylinder or located in the syringe cylinder itself, close to the cover. In this case, a lock is preferably included to prevent the agitation element from blocking the syringe outlet.

In addition, the recess may comprise an annular recess that is disposed in the cover of the syringe cylinder. This design eliminates the need to orient the agitation element with respect to the syringe when the latter has been completely emptied.

Preferably, the recess is arranged in the syringe plunger. In this case, careful attention should be paid to the accurate orientation of the plunger with respect to the magnetic field source, unless an annular recess is situated in that part of the plunger which faces toward the needle attachment end (i.e., distal end) of the syringe. Combinations of recesses on the plunger and, at the same time, at that end of the syringe which lies at the needle attachment are also conceivable.

An important feature of the syringe is the design of the plunger, the closure, and the corresponding distal opening.

The agitation element must be controlled in such a way that sufficient homogenization is ensured but the particles in the ultrasound contrast agent are not destroyed by transverse forces. The intensity and frequency of the movement has to be controlled, in accordance with the sensitivity of the ultrasound contrast agent and in accordance with the movement sequence, in such a way that the consistency of the particles in the ultrasound contrast agent is not adversely affected.

Turning now to the drawings of the preferred embodiments, FIG. 1 illustrates a syringe 1 having a plunger 2 movably disposed therein and a needle attachment or distal discharge end 3. The syringe 1 is removably connected to an injector 5 via a holder 4. Therefore, the syringe 1 can be inserted into the holder 4 in a reversible manner.

The injector 5 has a ram 6 which is removably connected to the plunger 2 of the syringe 1. The ram 6 is moved with respect to the housing of the injector 5 by a motor 7, the motor turning a ring 8 which has a screw thread and surrounds the ram 6, which likewise has a complementary screw thread. The ring 8 is rotatable with respect to the housing.

The housing of the injector 5 is connected to the stand 10 of the injector 5 via a joint 9. A rocker motor 11 allows relative movement between housing of the injector 5 and its stand 10. The movement of the rocker motor 11 is controlled by a control device 12. It is possible here to account individually for the nature of the contrast agent, the size of the syringe, the volume per minute of the injection and the stress of the patient.

At or near the distal end of the syringe 1, the syringe 1 includes a recess 13 for accommodating an agitation element 14, which is preferably in the form of a ball. Shortly before the syringe 1 has been completely emptied of its contents, the control device 12 adjusts the position of the syringe 1 in such a way that the ball 14 slides into the recess 13, thereby allowing the plunger 2 to be driven completely to the end of the syringe 1 in the direction of the needle attachment end 3 thereof.

FIG. 2 illustrates a syringe 1 having a plunger 2 movably disposed therein and a needle attachment or distal discharge end 3. The syringe 1 is removably connected to an injector 5 via a holder 4. Therefore, the syringe 1 can be inserted into the holder 4 in a reversible manner.

The injector 5 includes a ram 6 which is removably connected to the plunger 2 of the syringe 1. The ram 6 is moved with respect to the housing of the injector 5 by a motor 7, the motor turning a ring 8 which has a screw thread and surrounds the ram 6, which likewise has a complementary screw thread. The ring 8 is rotatable with respect to the housing.

The injector 5, as shown, preferably stands on an accessory 15 for the injector. This accessory 15 has a stand base 16 and a stand surface 17 which is connected to the stand base 16 via a pivot joint 18. A lifting motor 19 moves a linkage 20 which is designed in the form of scissors and is connected to the motor via a connecting rod 21. The movement is controlled by means of a control device 12.

In the end of the plunger 2 facing the distal discharge end 3 of the syringe 1, the plunger 2 includes a plunger recess 22 for accommodating an agitation element 14, which is preferably in the form of a ball. Shortly before the syringe 1 has been completely emptied of its contents, the control device 12 adjusts the position of the syringe 1 in such a way that the ball 14 slides into the plunger recess 22, thereby allowing the plunger 2 to be driven completely in the direction of the needle attachment 3 end thereof.

EXAMPLES

Example 1

A vibratory agitator was used to prevent phase separation in Levovist™ ultrasound contrast agent. The vibratory agitator includes a motor-driven vibrating unit and an electronic control unit containing a battery supply and controls for regulating the degree of vibration. The vibrating unit was connected mechanically to the syringe.

At low concentrations (e.g., 200 mg/ml), Levovist™ does not remain stable as a suspension for longer than 2–3 minutes. The suspension separates into two different phases: a liquid phase (which forms on the top of the agent) and a particle phase (which collects at the bottom). After resuspension, however, Levovist™ still provides optimal clinical results.

At a concentration of 300 mg/ml, Levovist™ separates into phases after 25–30 minutes, well above the Levovist™ approval limit of 10–15 minutes. At a concentration of 400 mg/ml, Levovist™ separates only after a matter of hours. Thus, for concentrations of 300 mg/ml and 400 mg/ml, no additional agitation is required to maintain Levovist™ in solution.

Test Setup

The vibratory agitator was tested with a 200 mg/ml concentration of Levovist™ using in-vitro Doppler measurement equipment. An IVAC P400 pump and a 20-ml Levovist™ syringe, which was connected directly to the vibratory agitator. To avoid vibration power loss, the pump's syringe holder was not connected to the syringe.

Testing Method

The trial consisted of three separate examinations without vibration and three with medium vibration power. The infusion flow settings were between 100 and 200 ml/h. Different flow settings only lead to differences ion the achievable Doppler intensity, not to differences in the (qualitative) curve form.

Test Results

Figure 6:
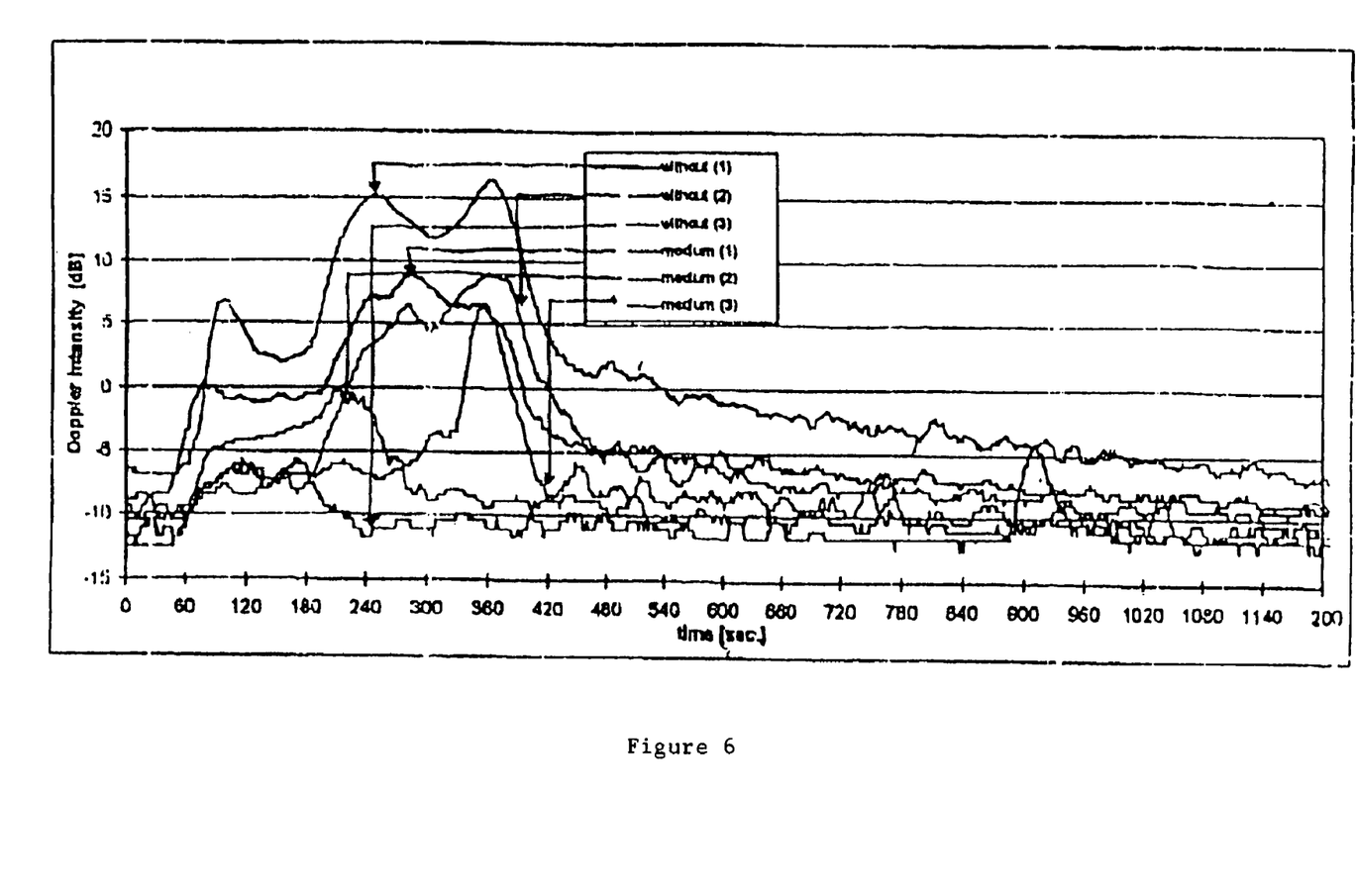
FIG. 6 is a graphical view comparing the Doppler signal intensity of a contrast agent with medium vibratory resuspension versus that of the contrast agent with no resuspension.

FIG. 6 illustrates the results of the tests in graphical form, which plots Doppler intensity (dB) versus time (Sec.). The graph in FIG. 6 shows (1) three trials without vibration; and (2) three trials with a constant medium vibration.

Without vibration, the typical suspension problems with Levovist™ at a concentration of 200 mg/ml are shown in FIG. 6. It is not possible to obtain a constant plateau phase of Doppler intensity. All of the non-vibration curves have more than one local maximum over time. Curve 3 does have a plateau, but only for one minute and at a low intensity level.

With vibration, plateau phases were achieved for the following durations: (1) Curve 1—2 minutes (70–190 sec.); (2) Curve 2—1.5 minutes (90–180 sec.); and (3) Curve 3—3 minutes (120–300 sec.).

However, the vibratory agitator did not provide a complete constant Doppler intensity plateau. In the vibratory curves, a second maximum with too strong an increase in Doppler intensity was observed. For example, second maximums occurred at the following times: (1) Curve 1—at 300 sec. and at plus 10 dB compared to the prior level; (2) Curve 2—at 200 sec. and at plus 8 dB compared to the prior level; and (3) Curve 3—at 350 sec. and at plus 14 dB compared to the prior level.

Example 2

The below examples use magnetic bars and ferromagnetic balls driven by a magnetic field to agitate or resuspend the contrast agents. While the examples do not use the mechanical devices disclosed herein, the results of increased and/or consistent enhancement properties for agitated or resuspended contrast agents may be considered independent of the means used to agitate or resuspend the contrast agents.

For Levovist™ 200 mg/ml ultrasound contrast fluid, which is manufactured by Schering AG of Berlin, Germany, phase separation occurs within a couple of minutes (approximately 3–5 minutes) after preparation. This phase separation is characterized by contrast particles aggregating at the lower part of a syringe containing the contrast fluid and the watery diluent collecting above the contrast particles within the syringe.

A number of technical approaches to mitigating and/or preventing Levovist™ phase separation were tested using a standardized laboratory model. In the first technical approach, a small ferromagnetic ball (having a higher specific weight then Levovist™) was placed in a syringe and moved therein by means of a magnetic field applied thereto. In the second technical approach, an agitation element (having a higher specific weight then Levovist™) was placed in the syringe and moved therein by means of an external magnetic bar moved outside of and relative to the syringe.

Test Setup

The tests were conducted using in-vitro test equipment validated to simulate in-vivo contrast enhancement conditions. The test equipment allowed reproducible measurements of the enhancement characteristics of ultrasound contrast fluid suspensions.

Through the controlled movement or control of a magnetic field source, agitation elements placed in the syringe were able to be moved in a controlled fashion to agitate the ultrasound contrast fluid to prevent phase separation. After agitation, the ultrasound contrast fluid was injected into the testing equipment using a transfer tube and a 22 G needle. The simulated body temperature was 37° C. and the simulated negative pressure of the lung simulating component (i.e., oxygenator) of the testing equipment was 100 mBar.

Testing Method

Respective measurements of the enhancement properties of the ultrasound contrast fluid suspension over a prolonged period of time (up to 22 minutes) were conducted for syringes having magnetic agitation elements and for syringes not incorporating magnetic agitation elements. A standard infusion/injection speed of 1 ml/min was used throughout the tests. The impact of the phase separation mitigation approaches were deducted from the variances in the measured Doppler-signal intensity.

Test Results—Test One

Figure 3:
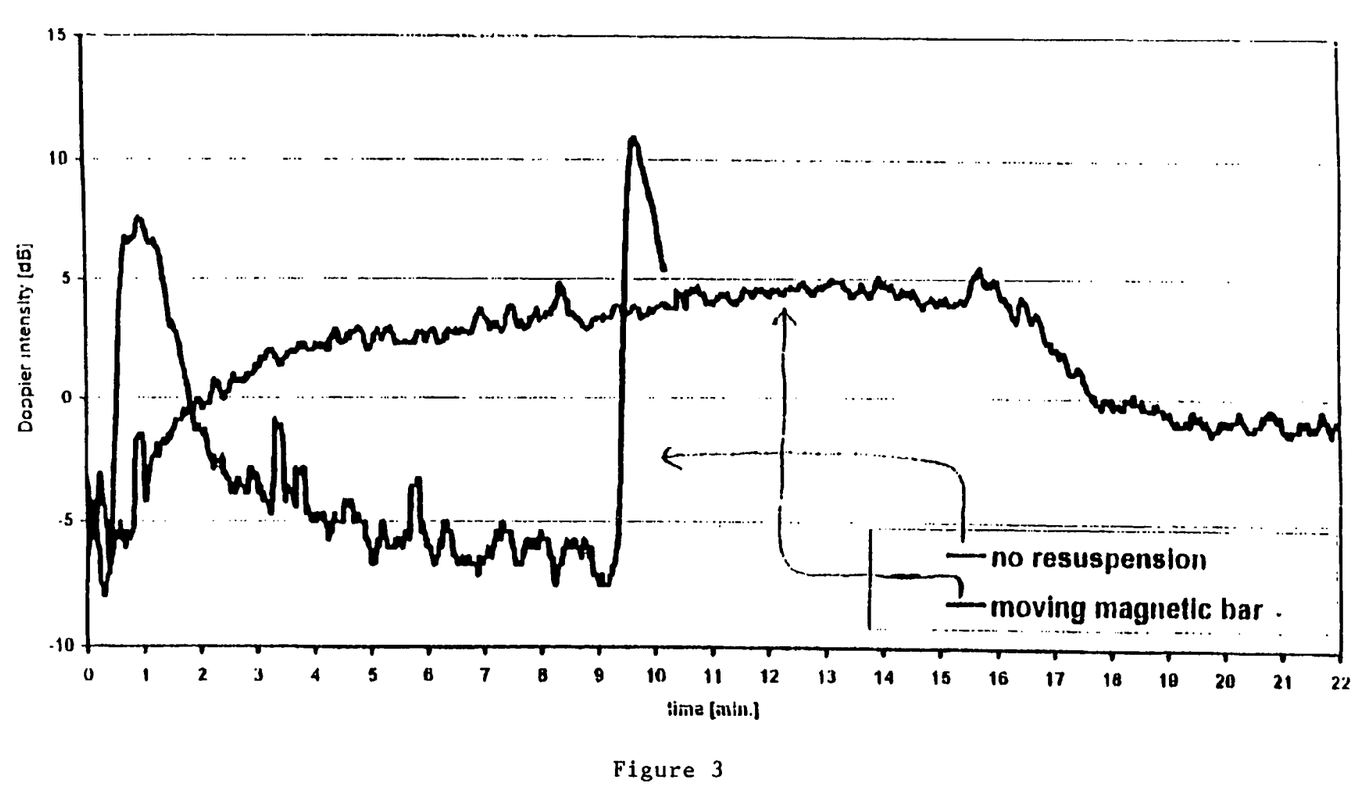
FIG. 3 is a graphical view comparing the Doppler signal intensity of a contrast agent with resuspension versus that of the contrast agent with no resuspension.

As shown in FIG. 3, no agitation of the ultrasound contrast fluid suspension leads to significant unfavorable inconsistencies in the enhancement properties of the contrast fluid, which is not suitable for clinical applications. However, when a magnetic bar was used to agitate the ultrasound contrast fluid suspension within the syringe, by means of a magnetic source located outside of the syringe, the contrast fluid was resuspended and a long-lasting, stable enhancement pattern was achieved.

Test Results—Test Two

Figure 4:
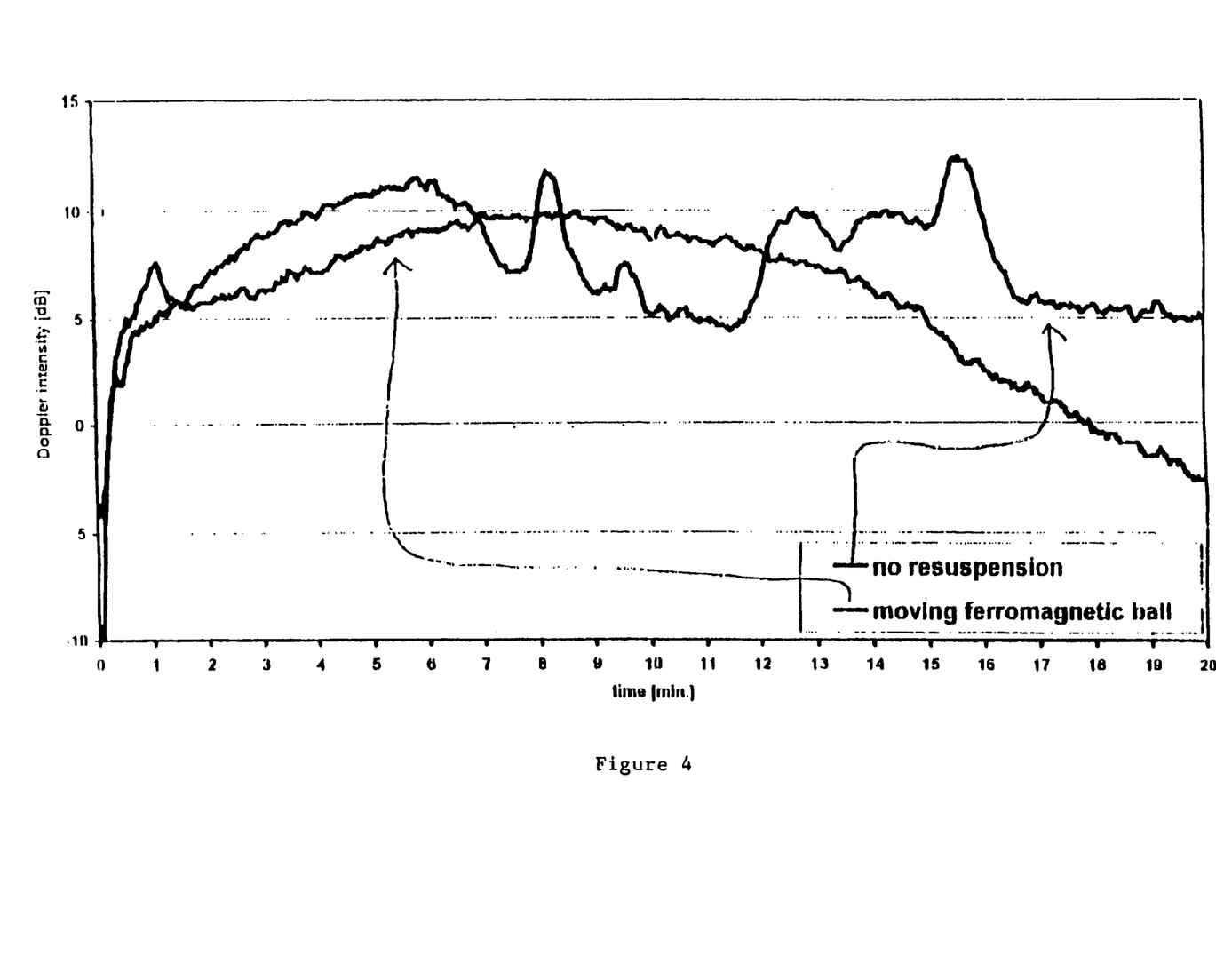
FIG. 4 is a graphical view comparing the Doppler signal intensity of a contrast agent with resuspension versus that of the contrast agent with no resuspension.

In this test, a ferromagnetic ball was moved within the syringe through application of an outside magnetic field. Again, as shown in FIG. 4, the test results clearly indicate that resuspension of the ultrasound contrast fluid suspension leads to significantly more consistent enhancement properties when compared to non-resuspended ultrasound contrast fluid suspension. With regard to the non-resuspended contrast fluid enhancement properties, the differences compared to Results—Test One (above) show that the extent and impact of phase separation on contrast enhancement is largely unpredictable.

Test Results—Test Three

Figure 5:
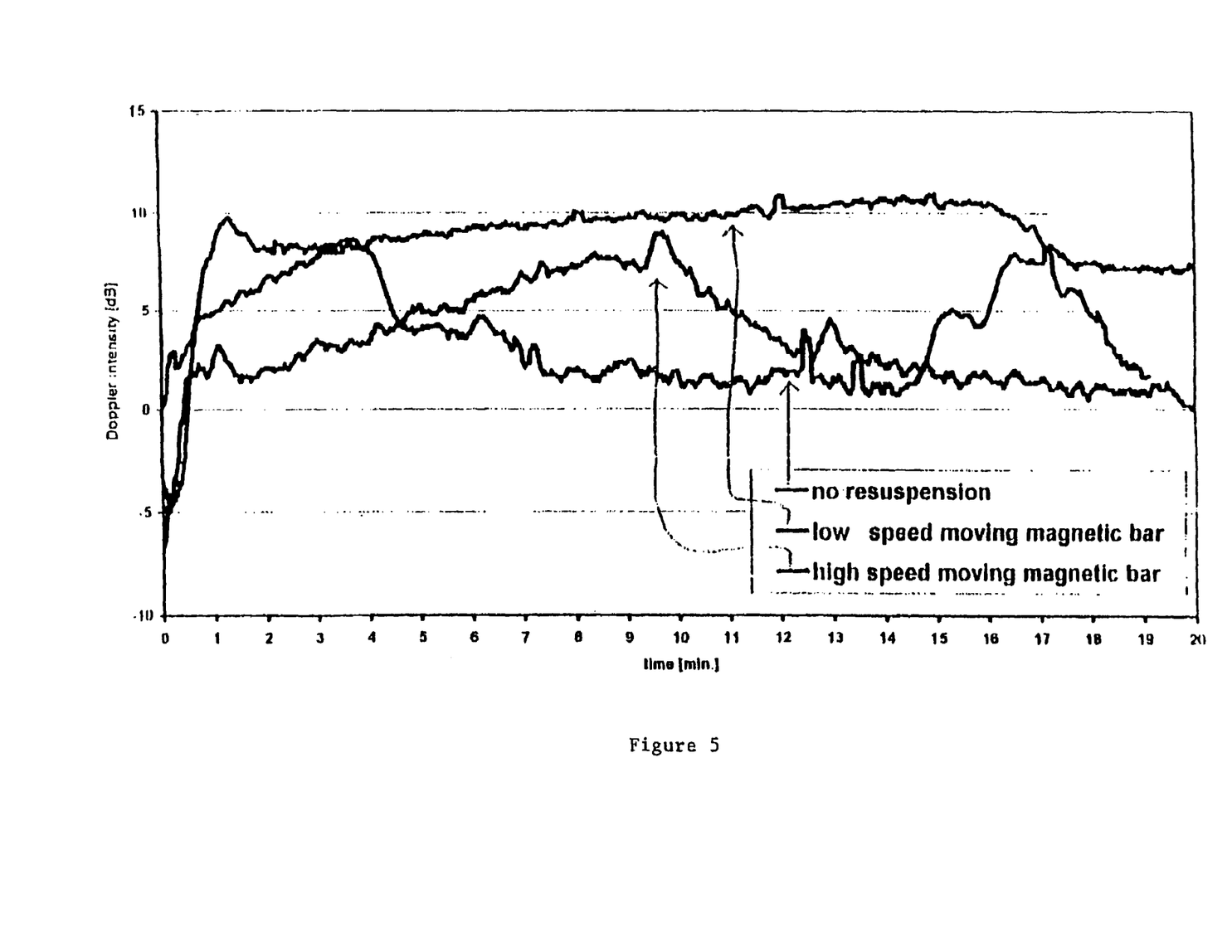
FIG. 5 is a graphical view comparing the Doppler signal intensity of a contrast agent with no resuspension versus that of the contrast agent with low-speed and high-speed resuspensions.

In this test, a magnetic bar was moved within the syringe through application of a ferromagnetic object outside the syringe. Besides a baseline comparison (i.e., compared to no resuspension of contrast fluid suspension), the influence of variations in the strength of the mechanical forces for resuspension were investigated. As can be clearly deducted from the test results, as shown in FIG. 5, ultrasound contrast fluid suspensions contain fragile particles and the mechanical forces applied for resuspension must therefore be adjusted to the stability and strength of the contrast fluid suspension. An extremely vigorous resuspension is detrimental for the enhancement properties of the contrast fluid, whereas a slight agitation may not prevent phase separation. The key is to adjust the resuspension mode in way that the forces impacting the contrast fluid particles do not impair or limit their contrast enhancement purpose. The level of mechanical force required and/or tolerable for each individual ultrasound contrast fluid, including Levovist™ varies, but a reproducible and controllable resuspension mode is required.

It should be appreciated that the present invention may be configured as appropriate for the application. The embodiments described above are to be considered in all respects only as illustrative and not restrictive. The scope of the invention is indicated by the following claims, rather than by the foregoing description. All changes which fall within the meaning and range of equivalency of the claims are to be embraced within their scope.

LIST OF REFERENCE NUMERALS

1 Syringe
2 Plunger
3 Needle attachment
4 Holder
5 Injector
6 Ram
7 Motor
8 Ring
9 Joint
10 Stand foot
11 Rocker motor
12 Control device
13 Bulge
14 Ball
15 Accessory
16 Stand base
17 Stand surface
18 Pivot joint
19 Lifting motor
20 Linkage
21 Connecting rod
22 Plunger bulge

What is claimed is:

1. A syringe comprising:
a body comprising a distal discharge end;
a plunger movably disposed within the body;
at least one agitation element comprising a casing and disposed within the body between the plunger and the distal discharge end, the at least one agitation element operable to agitate an ultrasound contrast fluid in the syringe when the syringe is moved to substantially maintain the homogeneity and integrity of the ultrasound contrast fluid without substantially impairing the diagnostic properties thereof; and
an annular recess defined in the plunger to accommodate the at least one agitation element.

2. The syringe of claim 1 wherein the at least one agitation element has a density different from that of the fluid contained within the syringe.

3. The syringe of claim 1 wherein the at least one agitation element comprises a solid.

4. The syringe of claim 3 wherein the at least one agitation element has a density greater than that of the fluid in the syringe.

5. The syringe of claim 1 wherein the at least one agitation element comprises a gas.

6. The syringe of claim 1, further comprising a recess defined in the body of the syringe, the recess operable to accommodate the at least one agitation element.

7. The syringe of claim 6 wherein the recess is defined adjacent to the distal discharge end of the syringe.

8. The syringe of claim 6 wherein the recess comprises an annular recess.

9. An injector system comprising:
   an injector comprising means for mounting a syringe thereon;
   a syringe comprising a body having a distal discharge end and means cooperable with the injector means for mounting the syringe on the injector, a plunger movably disposed within the body, and at least one agitation element disposed within the body between the plunger and the distal discharge end; and
   a movement mechanism operably associated with the injector, the movement mechanism operable to move the syringe such that the at least one agitation element agitates a fluid contained in the syringe.

10. The injector system of claim 9 wherein the fluid comprises a contrast agent.

11. The injector system of claim 10 wherein the contrast agent comprises an ultrasound contrast agent.

12. The injector system of claim 11, further comprising a control device operably associated with the movement mechanism, the control device operable to control the movement of the syringe induced by the movement mechanism to substantially maintain the homogeneity and integrity of the ultrasound contrast agent without substantially impairing the diagnostic properties thereof.

13. The injector system of claim 12 wherein the control device is operable to control the intensity and/or frequency of the movement of the syringe.

14. The injector system of claim 9 wherein the at least one agitation element has a density different from that of the fluid contained within the syringe.

15. The injector system of claim 9 wherein the at least one agitation element comprises a solid.

16. The injector system of claim 15 wherein the at least one agitation element has a density greater than that of the fluid in the syringe.

17. The injector system of claim 9 wherein the at least one agitation element comprises a gas.

18. The injector system of claim 17 wherein the at least one agitation element is surrounded by a cover.

19. The injector system of claim 9 wherein the movement mechanism moves the syringe in one or more of circular, partially circular and linear motions.

20. The injector system of claim 9 wherein the movement mechanism moves the syringe in a rotational motion.

21. The injector system of claim 9, further comprising a recess defined in the body of the syringe, the recess operable to accommodate the at least one agitation element.

22. The injector system of claim 21 wherein the recess is defined adjacent to the distal discharge end of the syringe.

23. The injector system of claim 21 wherein the recess comprises an annular recess.

24. The injector system of claim 9, further comprising a recess defined in the plunger of the syringe, the recess operable to accommodate the at least one agitation element.

25. The injector system of claim 24 wherein the recess comprises an annular recess.

26. The injector system of claim 9, further comprising a control device operably associated with the movement mechanism, the control device operable to control the movement of the syringe induced by the movement mechanism.

27. The injector system of claim 9 wherein the movement mechanism comprises a motor.

28. The injector system of claim 9 wherein the movement mechanism comprises an accessory comprising a base, a surface connected to the base via a pivot joint, a motor and a linkage connected between the motor and the base and the surface.

29. The injector system of claim 9 wherein the movement mechanism comprises a vibratory agitator.

30. The injector system of claim 9 wherein the movement mechanism is connected to the syringe.

31. A method for agitating the contents of a syringe, comprising:
   providing an injector comprising means for mounting a syringe thereon;
   providing a syringe comprising a body having a distal discharge end and means cooperable with the injector means for mounting the syringe on the injector, a plunger movably disposed within the body, and at least one agitation element disposed within the body between the plunger and the distal discharge end;
   providing a movement mechanism operably associated with the injector, the movement mechanism operable to move the syringe such that the at least one agitation element agitates a fluid contained in the syringe;
   activating the movement mechanism to move the syringe; and
   agitating the fluid in the syringe with the at least one agitation element.

32. The method of claim 31, further comprising the step of deactivating the movement mechanism to terminate the agitation of the syringe contents.

33. The method of claim 31 wherein the movement mechanism is connected to the syringe.

34. A syringe comprising:
   a body comprising a distal discharge end;
   a plunger movably disposed within the body;
   at least one agitation element comprising a gas surrounded by a cover and disposed within the body between the plunger and the distal discharge end, the at least one agitation element operable to agitate an ultrasound contrast fluid in the syringe when the syringe is moved to substantially maintain the homogeneity and integrity of the ultrasound contrast fluid without substantially impairing the diagnostic properties thereof; and
   an annular recess defined in the body or the plunger to accommodate the at least one agitation element.

35. The syringe of claim 34 wherein the at least one agitation element has a density different from that of the fluid contained within the syringe.

36. The syringe of claim 34 wherein the recess is defined in the body of the syringe adjacent to the distal discharge end thereof.

37. A syringe comprising:
   a body comprising a distal discharge end;
   a plunger movably disposed within the body;
   at least one agitation element disposed within the body between the plunger and the distal discharge end, the at least one agitation element operable to agitate a fluid in the syringe; and
   an annular recess defined in the body of the syringe, the annular recess operable to accommodate the at least one agitation element.

38. The syringe of claim 37 wherein the fluid comprises a contrast agent.

39. The syringe of claim 38 wherein the contrast agent comprises an ultrasound contrast agent.

40. The syringe of claim 37 wherein the at least one agitation element has a density different from that of the fluid contained within the syringe.

41. The syringe of claim 37 wherein the at least one agitation element comprises a solid.

42. The syringe of claim 41 wherein the at least one agitation element has a density greater than that of the fluid in the syringe.

43. The syringe of claim 37 wherein the at least one agitation element comprises a gas.

44. The syringe of claim 43 wherein the at least one agitation element is surrounded by a cover.

45. The syringe of claim 37 wherein the at least one agitation element comprises a casing.

46. An injector system comprising:
   an injector comprising a syringe mounting device;
   a syringe comprising:
      a body comprising a distal discharge end and an injector attachment device cooperable with the syringe mounting device for mounting the syringe on the injector;
      a plunger movably disposed within the body; and
      at least one agitation element disposed within the body between the plunger and the distal discharge end; and
   a movement mechanism operably associated with the injector, the movement mechanism operable to move the syringe such that the at least one agitation element agitates a fluid contained in the syringe.

47. The injector system of claim 46 wherein the fluid comprises a contrast agent.

48. The injector system of claim 47 wherein the contrast agent comprises an ultrasound contrast agent.

49. The injector system of claim 48, further comprising a control device operably associated with the movement mechanism, the control device operable to control the movement of the syringe induced by the movement mechanism to substantially maintain the homogeneity and integrity of the ultrasound contrast agent without substantially impairing the diagnostic properties thereof.

50. The injector system of claim 49 wherein the control device is operable to control the intensity and/or frequency of the movement of the syringe.

51. The injector system of claim 46 wherein the at least one agitation element has a density different from that of the fluid contained within the syringe.

52. The injector system of claim 46 wherein the at least one agitation element comprises a solid.

53. The injector system of claim 52 wherein the at least one agitation element has a density greater than that of the fluid in the syringe.

54. The injector system of claim 46 wherein the at least one agitation element comprises a gas.

55. The injector system of claim 54 wherein the at least one agitation element is surrounded by a cover.

56. The injector system of claim 46 wherein the movement mechanism moves the syringe in one or more of circular, partially circular and linear motions.

57. The injector system of claim 46 wherein the movement mechanism moves the syringe in a rotational motion.

58. The injector system of claim 46, further comprising a recess defined in at least one of the body of the syringe and the plunger of the syringe, the recess operable to accommodate the at least one agitation element.

59. The injector system of claim 58 wherein the recess is defined in the body of the syringe adjacent to the distal discharge end thereof.

60. The injector system of claim 58 wherein the recess is defined in the plunger of the syringe.

61. The injector system of claim 58 wherein the recess comprises an annular recess.

62. The injector system of claim 46, further comprising a control device operably associated with the movement mechanism, the control device operable to control the movement of the syringe induced by the movement mechanism.

63. The injector system of claim 46 wherein the movement mechanism comprises a motor.

64. The injector system of claim 46 wherein the movement mechanism comprises an accessory comprising a base, a surface connected to the base via a pivot joint, a motor and a linkage connected between the motor and the base and the surface.

65. The injector system of claim 46 wherein the movement mechanism comprises a vibratory agitator.

66. The injector system of claim 46 wherein the movement mechanism is connected to the syringe.

67. An injector system comprising:
   an injector comprising a syringe mounting device;
   a syringe comprising:
      a body comprising a distal discharge end and an injector attachment device cooperable with the syringe mounting device for mounting the syringe on the injector;
      a plunger movably disposed within the body; and
      at least one agitation element disposed within the body between the plunger and the distal discharge end; and
   a movement mechanism operably associated with the injector, the movement mechanism operable to rotate the syringe such that the at least one agitation element agitates a fluid contained in the syringe.

68. The injector system of claim 67 wherein the fluid comprises a contrast agent.

69. The injector system of claim 68 wherein the contrast agent comprises an ultrasound contrast agent.

70. The injector system of claim 69, further comprising a control device operably associated with the movement mechanism, the control device operable to control the rotation of the syringe induced by the movement mechanism to substantially maintain the homogeneity and integrity of the ultrasound contrast agent without substantially impairing the diagnostic properties thereof.

71. The injector system of claim 70 wherein the control device is operable to control the intensity and/or frequency of the movement of the syringe.

72. The injector system of claim 67 wherein the at least one agitation element has a density different from that of the fluid contained within the syringe.

73. The injector system of claim 67 wherein the at least one agitation element comprises a solid.

74. The injector system of claim 73 wherein the at least one agitation element has a density greater than that of the fluid in the syringe.

75. The injector system of claim 67 wherein the at least one agitation element comprises a gas.

76. The injector system of claim 75 wherein the at least one agitation element is surrounded by a cover.

77. The injector system of claim 67 wherein the movement mechanism is further operable to move the syringe in one or more of circular, partially circular and linear motions.

78. The injector system of claim 67, further comprising a recess defined in at least one of the body of the syringe and the plunger of the syringe, the recess operable to accommodate the at least one agitation element.

79. The injector system of claim 78 wherein the recess is defined in the body of the syringe adjacent to the distal discharge end thereof.

80. The injector system of claim 78 wherein the recess is defined in the plunger of the syringe.

81. The injector system of claim 78 wherein the recess comprises an annular recess.

82. The injector system of claim 67, further comprising a control device operably associated with the movement mechanism, the control device operable to control the rotation of the syringe induced by the movement mechanism.

83. The injector system of claim 67 wherein the movement mechanism comprises a motor.

84. The injector system of claim 67 wherein the movement mechanism comprises an accessory comprising a base, a surface connected to the base via a pivot joint, a motor and a linkage connected between the motor and the base and the surface.

85. The injector system of claim 67 wherein the movement mechanism comprises a vibratory agitator.

86. An injector system comprising:
   an injector comprising a syringe mounting device;
   a syringe comprising:
      a body comprising a distal discharge end, an injector attachment device cooperable with the syringe mounting device for mounting the syringe on the injector, and a recess defined therein;
      a plunger movably disposed within the body; and
      at least one agitation element disposed within the body between the plunger and the distal discharge end, the recess operable to accommodate the at least one agitation element; and
   a movement mechanism operably associated with the injector, the movement mechanism operable to move the syringe such that the at least one agitation element agitates a fluid contained in the syringe.

87. The injector system of claim 86 wherein the fluid comprises a contrast agent.

88. The injector system of claim 87 wherein the contrast agent comprises an ultrasound contrast agent.

89. The injector system of claim 88, further comprising a control device operably associated with the movement mechanism, the control device operable to control the movement of the syringe induced by the movement mechanism to substantially maintain the homogeneity and integrity of the ultrasound contrast agent without substantially impairing the diagnostic properties thereof.

90. The injector system of claim 89 wherein the control device is operable to control the intensity and/or frequency of the movement of the syringe.

91. The injector system of claim 86 wherein the at least one agitation element has a density different from that of the fluid contained within the syringe.

92. The injector system of claim 86 wherein the at least one agitation element comprises a solid.

93. The injector system of claim 92 wherein the at least one agitation element has a density greater than that of the fluid in the syringe.

94. The injector system of claim 86 wherein the at least one agitation element comprises a gas.

95. The injector system of claim 94 wherein the at least one agitation element is surrounded by a cover.

96. The injector system of claim 86 wherein the movement mechanism moves the syringe in one or more of circular, partially circular and linear motions.

97. The injector system of claim 86 wherein the movement mechanism moves the syringe in a rotational motion.

98. The injector system of claim 86 wherein the recess is located adjacent to the distal discharge end of the syringe.

99. The injector system of claim 86 wherein the recess comprises an annular recess.

100. The injector system of claim 86, further comprising a control device operably associated with the movement mechanism, the control device operable to control the movement of the syringe induced by the movement mechanism.

101. The injector system of claim 86 wherein the movement mechanism comprises a motor.

102. The injector system of claim 86 wherein the movement mechanism comprises an accessory comprising a base, a surface connected to the base via a pivot joint, a motor and a linkage connected between the motor and the base and the surface.

103. The injector system of claim 86 wherein the movement mechanism comprises a vibratory agitator.

104. A method for agitating the contents of a syringe comprising a body having a distal discharge end, a plunger movably disposed within the body and at least one agitation element disposed within the body between the plunger and the distal discharge end, the method comprising:
   providing a movement mechanism operably associated with an injector to which the syringe is mounted, the movement mechanism operable to move the syringe such that the at least one agitation element agitates a fluid contained in the syringe;
   activating the movement mechanism to move the syringe; and
   agitating the fluid in the syringe with the at least one agitation element.

105. The method of claim 104, further comprising:
   deactivating the movement mechanism to terminate the agitation of the syringe contents.

106. The method of claim 104 wherein the contents of the syringe comprise a contrast agent.

107. The method of claim 104 wherein the movement mechanism rotates the syringe.

108. The method of claim 104 wherein the syringe further comprises a recess defined in at least one of the body of the syringe and the plunger of the syringe, the recess operable to accommodate the at least one agitation element.

109. The method of claim 108 wherein the recess is defined in the body of the syringe adjacent to the distal discharge end thereof.

110. The method of claim 108 wherein the recess comprises an annular recess.

111. The method of claim 104 wherein the movement mechanism is connected to the syringe.

* * * * *